US008622981B2

(12) United States Patent
Hartwell et al.

(10) Patent No.: US 8,622,981 B2
(45) Date of Patent: Jan. 7, 2014

(54) MODULAR WOUND TREATMENT APPARATUS WITH RELEASABLE CLIP CONNECTION

(75) Inventors: Edward Hartwell, York (GB); Carl Saxby, York (GB)

(73) Assignee: Smith & Nephew PLC, London (GB)

( * ) Notice: Subject to any disclaimer, the term of this patent is extended or adjusted under 35 U.S.C. 154(b) by 636 days.

(21) Appl. No.: 12/667,227

(22) PCT Filed: Jun. 27, 2008

(86) PCT No.: PCT/GB2008/050508
§ 371 (c)(1),
(2), (4) Date: Dec. 29, 2009

(87) PCT Pub. No.: WO2009/004368
PCT Pub. Date: Jan. 8, 2009

(65) Prior Publication Data
US 2010/0185164 A1 Jul. 22, 2010

(30) Foreign Application Priority Data
Jul. 2, 2007 (GB) .................................. 0712737.6

(51) Int. Cl.
*A61M 1/00* (2006.01)
(52) U.S. Cl.
USPC ........... 604/313; 604/257; 604/259; 604/260; 604/317; 604/319; 604/320; 604/321; 604/322; 604/323; 417/4; 417/36; 417/37; 417/38; 417/39; 128/912; 210/85; 210/86; 210/91; 210/97; 210/104

(58) Field of Classification Search
USPC .................. 604/317, 319, 320, 321, 322, 323
See application file for complete search history.

(56) References Cited

U.S. PATENT DOCUMENTS

| 3,295,576 A | 1/1967 | Schmitt et al. |
|---|---|---|
| 4,112,949 A | 9/1978 | Rosenthal et al. |
| 4,250,882 A | 2/1981 | Adair |
| 4,569,674 A | 2/1986 | Phillips et al. |

(Continued)

FOREIGN PATENT DOCUMENTS

| DE | 1000684 B | 1/1957 |
|---|---|---|
| DE | 3431426 A1 | 7/1985 |

(Continued)

OTHER PUBLICATIONS

International Search Report mailed Oct. 21, 2008 for International Application No. PCT/GB2008/050508 in 6 pages.

(Continued)

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

Apparatus (200) for the application of topical negative pressure therapy to a user of the apparatus (200) is described together with a method for protecting said apparatus (200) when subjected to abnormal stresses, the apparatus (200) comprising a device (202) and a waste canister (204) releasably connected thereto wherein the device (202) and waste canister (204) are connected together by clip means (222), said clip means (222) being subject to failure upon application of abnormal stresses thereby permitting separation of the device (202) and waste canister (204).

30 Claims, 9 Drawing Sheets

(56) References Cited

U.S. PATENT DOCUMENTS

| | | |
|---|---|---|
| 4,758,220 A | 7/1988 | Sundblom et al. |
| 4,969,880 A | 11/1990 | Zamierowski |
| 5,096,385 A | 3/1992 | Georgi et al. |
| 5,466,229 A * | 11/1995 | Elson et al. .................... 604/317 |
| 5,527,293 A | 6/1996 | Zamierowski |
| 5,636,643 A | 6/1997 | Argenta et al. |
| 5,645,081 A | 7/1997 | Argenta et al. |
| 5,738,656 A | 4/1998 | Wagner |
| 6,071,267 A | 6/2000 | Zamierowski |
| 6,117,111 A | 9/2000 | Fleischmann |
| 6,142,982 A | 11/2000 | Hunt et al. |
| 6,345,623 B1 | 2/2002 | Heaton et al. |
| 6,648,862 B2 | 11/2003 | Watson |
| 6,685,681 B2 | 2/2004 | Lockwood et al. |
| 6,752,794 B2 | 6/2004 | Lockwood et al. |
| 6,764,462 B2 | 7/2004 | Risk, Jr. et al. |
| 6,824,533 B2 | 11/2004 | Risk, Jr. et al. |
| 6,936,037 B2 | 8/2005 | Bubb et al. |
| 7,004,915 B2 | 2/2006 | Boynton et al. |
| 7,022,113 B2 | 4/2006 | Lockwood et al. |
| 7,108,683 B2 | 9/2006 | Zamierowski |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,381,859 B2 | 6/2008 | Hunt et al. |
| 7,438,705 B2 | 10/2008 | Karpowicz et al. |
| D587,901 S | 3/2009 | Pidgeon et al. |
| 7,534,927 B2 | 5/2009 | Lockwood et al. |
| 7,553,306 B1 | 6/2009 | Hunt et al. |
| D602,582 S | 10/2009 | Pidgeon et al. |
| D602,583 S | 10/2009 | Pidgeon et al. |
| D602,584 S | 10/2009 | Pidgeon et al. |
| 7,604,610 B2 | 10/2009 | Shener et al. |
| 7,611,500 B1 | 11/2009 | Lina et al. |
| D607,202 S | 1/2010 | Pidgeon et al. |
| D617,094 S | 6/2010 | Pidgeon et al. |
| 7,763,000 B2 | 7/2010 | Risk, Jr. et al. |
| 7,780,201 B2 | 8/2010 | Luzbetak et al. |
| D625,801 S | 10/2010 | Pidgeon et al. |
| 7,846,141 B2 | 12/2010 | Weston |
| D630,313 S | 1/2011 | Pidgeon et al. |
| D630,725 S | 1/2011 | Pidgeon et al. |
| D645,137 S | 9/2011 | Gonzalez |
| D650,894 S | 12/2011 | Gonzalez |
| 2003/0163101 A1 | 8/2003 | Say |
| 2004/0249353 A1 | 12/2004 | Risks, Jr. et al. |
| 2007/0179460 A1 | 8/2007 | Adahan |
| 2007/0219532 A1 | 9/2007 | Karpowicz et al. |
| 2007/0292276 A1 | 12/2007 | Stutz et al. |
| 2009/0157016 A1 | 6/2009 | Adahan |
| 2009/0240218 A1 | 9/2009 | Braga et al. |
| 2010/0042021 A1 | 2/2010 | Hu et al. |
| 2010/0063464 A1 | 3/2010 | Meyer et al. |
| 2010/0106116 A1 | 4/2010 | Simmons et al. |
| 2010/0185165 A1 | 7/2010 | Middleton et al. |
| 2010/0187065 A1 | 7/2010 | Pidgeon et al. |
| 2010/0207768 A1 | 8/2010 | Pidgeon et al. |
| 2010/0228205 A1 | 9/2010 | Hu et al. |
| 2010/0244780 A1 | 9/2010 | Turner et al. |
| 2011/0008179 A1 | 1/2011 | Turner et al. |
| 2011/0054810 A1 | 3/2011 | Turner et al. |
| 2012/0001762 A1 | 1/2012 | Turner et al. |

FOREIGN PATENT DOCUMENTS

| | | |
|---|---|---|
| EP | 0777504 | 10/1998 |
| EP | 0688189 B2 | 9/2000 |
| EP | 0853950 | 10/2002 |
| EP | 1219311 | 7/2004 |
| EP | 1440667 B1 | 7/2004 |
| EP | 1171065 B1 | 3/2007 |
| GB | 2336546 B | 6/2000 |
| JP | H03-11106 | 2/1991 |
| JP | H06-58150 | 8/1994 |
| JP | H06-339495 | 12/1994 |
| JP | H08-320006 | 12/1996 |
| WO | WO 92/10983 | 7/1992 |
| WO | WO 96/05873 * | 8/1994 |
| WO | WO96/05873 | 2/1996 |
| WO | WO 096/05878 | 2/1996 |
| WO | WO 03/074106 * | 2/2003 |
| WO | WO 03/074106 | 9/2003 |
| WO | WO 2006/105892 | 10/2006 |
| WO | WO 2006/135934 | 12/2006 |
| WO | WO 2007/013064 A | 2/2007 |
| WO | WO 2007/024230 A | 3/2007 |
| WO | WO 2007/030599 A | 3/2007 |
| WO | WO 2007/087808 | 8/2007 |
| WO | WO 2008/039223 | 4/2008 |
| WO | WO 2008/039314 | 4/2008 |
| WO | WO 2010/051069 | 5/2010 |

OTHER PUBLICATIONS

Written Opinion of the International Searching Authority mailed Jan. 2, 2010 for International Application No. PCT/GB2008/050508 in 5 pages.

* cited by examiner

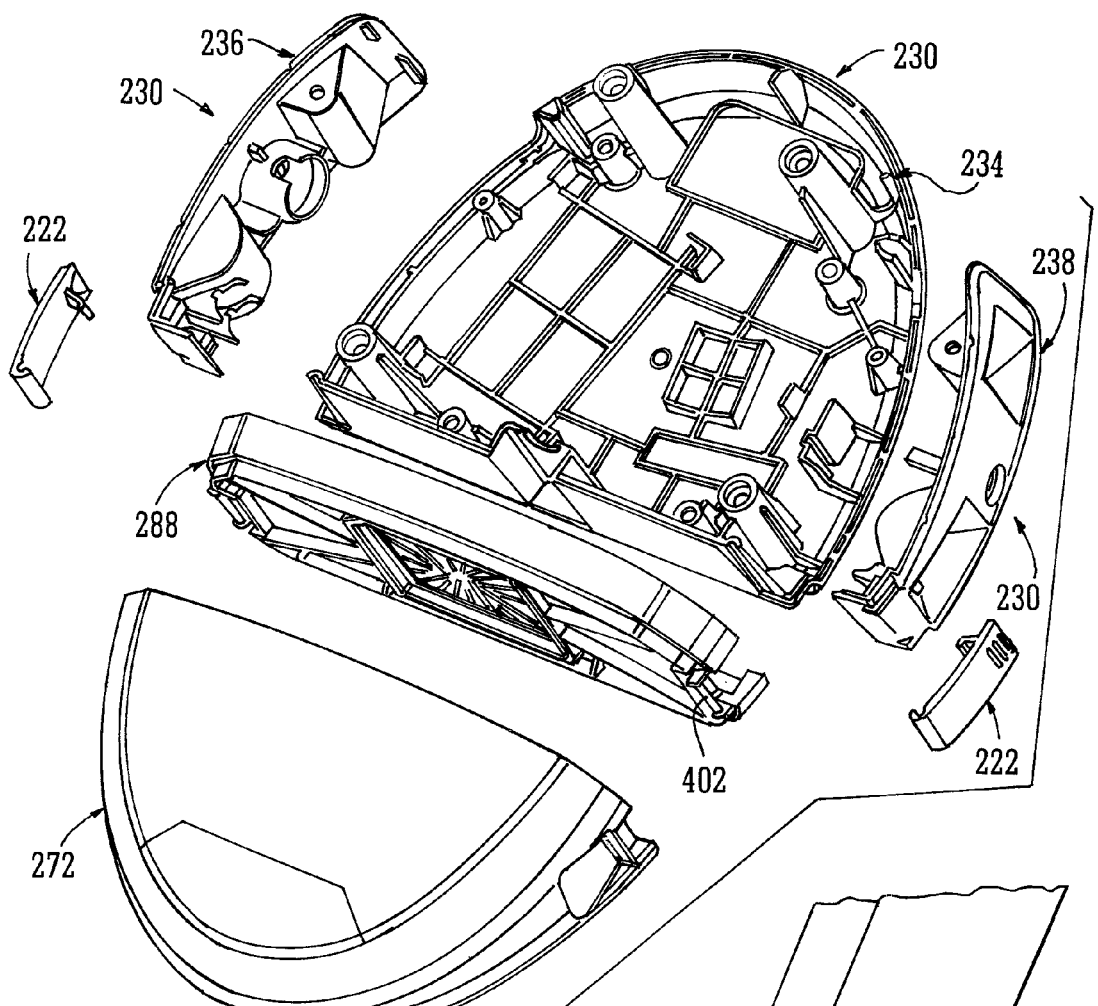
FIG. 10
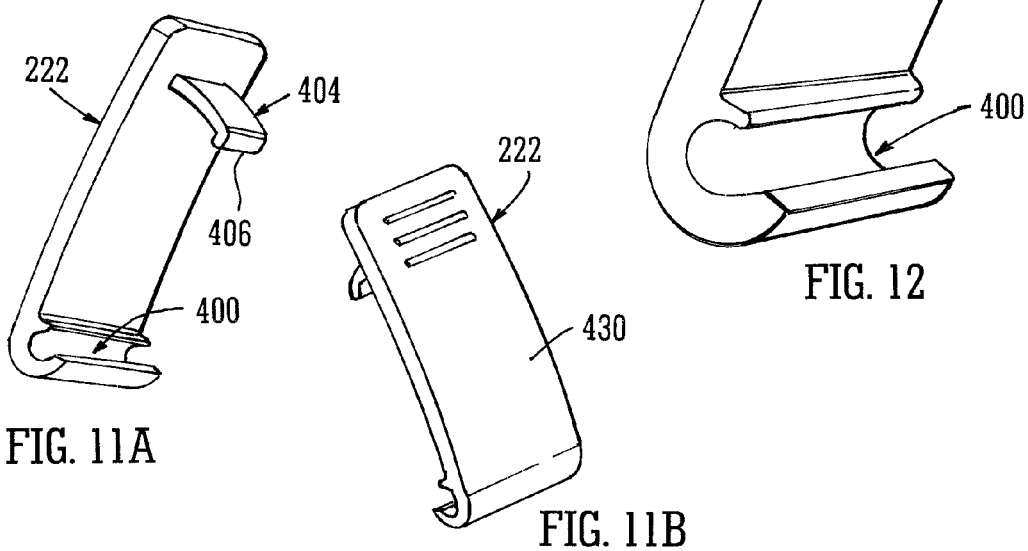
FIG. 11A
FIG. 11B
FIG. 12

MODULAR WOUND TREATMENT APPARATUS WITH RELEASABLE CLIP CONNECTION

The present invention relates to apparatus and a method for the application of topical negative pressure (TNP) therapy to wounds. In particular, but not exclusively, the present invention relates to features of apparatus and a method to prevent or minimise damage when subjected to conditions outside of normal operating conditions.

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to belt or harness. The unit embodies a device having mechanical and electrical/electronic functions and components and comprises an all enveloping casing in which the above components are housed and which casing also contains a waste canister. Should the unit be dropped, for example, or subjected to loads or impacts outside of normal operating conditions, all components thereof are subject thereto and serious damage may occur to the more expensive mechanical and/or electronic components. A further disadvantage of the apparatus described is the difficulty of removing and changing the waste canister, especially for less dextrous people. It is an aim of the present invention to at least partly mitigate the above-mentioned problems.

It is an aim of embodiments of the present invention to protect the more expensive parts of the apparatus from damage when used subjected to conditions outside of normal operating conditions.

It is a further aim of the present invention to provide apparatus where the waste canister is more easily accessible and more easily changed or replaced with a fresh canister.

According to a first aspect of the present invention there is provided apparatus for the application of topical negative pressure therapy to a user of the apparatus, the apparatus comprising a device and a waste canister releasably connected thereto wherein the device and waste canister are connected together by clip means.

The clip means are intended to fail upon the application of stresses outside of normal operating conditions, as further explained in more detail hereinbelow, upon which failure permits separation of the device and waste canister.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, foam, inflatable bladder or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In the present invention "normal" operating conditions would include use such as a patient or user sitting, walking or running with the apparatus on their person; sleeping and rolling onto the apparatus; accidentally letting the apparatus fall onto a soft surface such as a bed or carpeted floor, for example. The apparatus is intended to remain unaffected when, for example, it is hanging or fixed on a bedstead and able to withstand a pull force on the aspirant conduit or power lead not exceeding about 40N and preferably not exceeding about 20N.

In the present invention, the conditions which are considered to be abnormal or outside of normal operating conditions may include dropping of the apparatus onto the ground, impact when being worn by a patient when, for example, walking into an obstruction or falling down, or when the aspirant conduit or power lead is subject to an accidental tug causing the device to fall from a table or bed. Essentially, the present invention permits the device and waste canister to separate by failure of the clip means when the apparatus is subjected to abnormal stresses or impacts. The term "failure" in respect of the clip means shall be taken to means that the engaging features, which features may be present on the clip means themselves, on the device and/or on the waste canister, which the clip means couple with under normal conditions of connecting the device and waste canister together become disengaged without breakage or the clip means themselves suffer breakage of a feature thereof.

It is important that the separation of the device and waste canister occurs by disengagement of the clips means in some manner from the device rather than the waste canister. Thus, no damage is caused to the device and, if clip member breakage occurs then the user is not faced with having to remove a broken clip member from the relatively more delicate device unit. On disengagement, any damage to the waste canister can be rectified simply by the user fitting a new waste canister.

When, for example, the apparatus is dropped onto a hard surface the clip means fail as defined hereinabove thus allowing the device unit and waste canister to separate thus saving the device unit from sustaining significant damage such that would impair its operation. The invention is this, in effect, a shock absorbing measure.

In general the clip means may be able to withstand forces up to about 100N before failure thereof thus, a force or load of greater than about 100N in a direction tending to separate the device and waste canister may result in failure of the clip means holding the device and waste canister together. It is pointed out that forces tending to separate the device and waste canister may not necessarily be in mutually opposed directions but may be in other direction such as, for example, a force applied transversely on the waste canister tending to knock it sideways relative to the device unit.

In a preferred embodiment of the present invention the clip means in the form of clips made of stiff but resilient material are primarily attached to the waste canister on which they may be rotated through an arc about an axis provided by a location shaft on the waste canister. The clips may be releasably attached to the waste canister and in effect be consumer replaceable items which may be easily replaced upon breakage thereof so that the waste canister may be quickly reattached to the device. Thus, not only is the device protected from damage but also the waste canister itself.

In one embodiment of the present invention, the clips may be moulded from a POM (polyoxymethylene) acetal polymer, however, any suitable plastics material having adequate resilience may be employed. Although plastics materials are specifically mentioned since they are easily formed, suitable metal items would also fulfil the requirement.

In a preferred embodiment of the present invention, an end portion of the clip which attaches to the waste canister may comprise a deformable C-section recess so as to provide a snap-fit on a shaft portion on the waste canister. Intermediate the ends of the clip on an inwardly turned face there may be a resiliently deformable finger feature which engages with one or more co-operating features on the device unit to connect the device and waste canister together in functional engagement. Since the waste canister is a disposable item when full the clips may be disengaged from the device and the waste canister disposed of a fresh canister installed.

The clip surface may also be provided with so-called grip strips to assist the user in engaging the device and waste canister together.

The clips may be universal in that one design fits both sides of the apparatus or may be handed.

According to a second aspect of the present invention there is provided a method of protecting apparatus for the application of topical negative pressure to a user, the apparatus comprising a device and a waste canister releasably connected together, the method comprising the steps of providing clip means to connect the device and waste canister together and providing features on at least two of: said clip means; said device; and, said waste canister to permit separation of the device and waste canister in the event of failure of the clip means.

The features referred to may be points of intended failure by breakage on the clip means. Such features may comprise a reduced section portion or portions on the clip members or by moulded-in fracture lines, for example.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 mmHg to −80 mmHg, or −50 to −76 mmHg, or −50 to −75 mmHg as examples. The control system may also advantageously be able to maintain the set pressure within a tolerance band of +/− 10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus from the carry case.

The carry case may be provided with an aperture covered by a displaceable flap to enable user access to a keypad for varying the therapy applied by the apparatus.

In order that the present invention may be more fully understood, examples will now be described by way of illustration only with reference to the accompanying drawings, of which:

FIG. 10 shows an exploded view of casing features, waste canister parts having an embodiment according to the present invention;

FIGS. 11A and 11B show perspective views an inner surface of a left-hand clip and an outer surface of a right-hand clip, respectively of the embodiment shown in FIG. 10;

FIG. 12 shows an enlarged detail of one of the frangible clips of FIG. 11;

Figure 1:
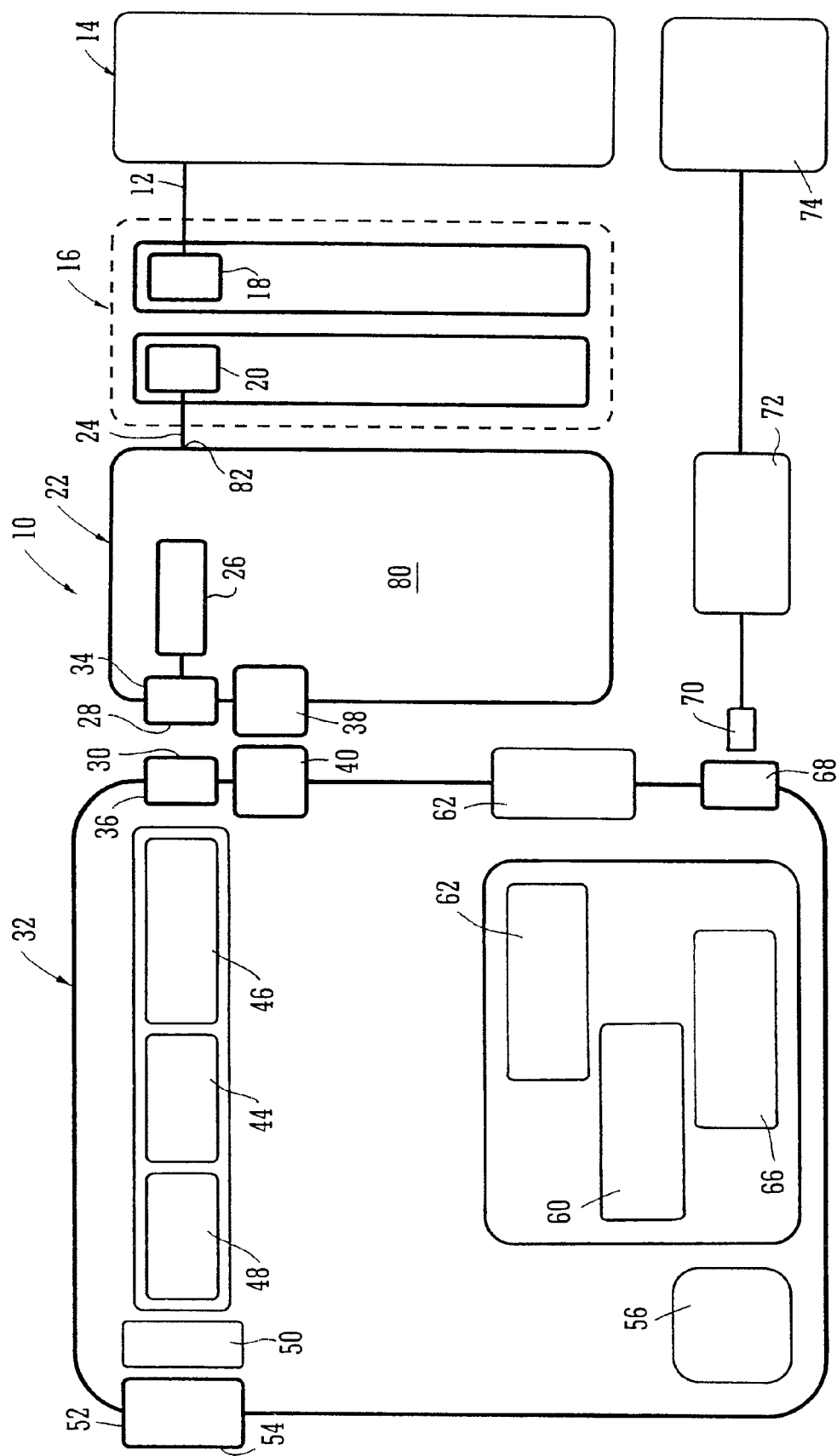
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well known materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 μm hydrophobic liquid filter and a 0.2 μm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the a control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
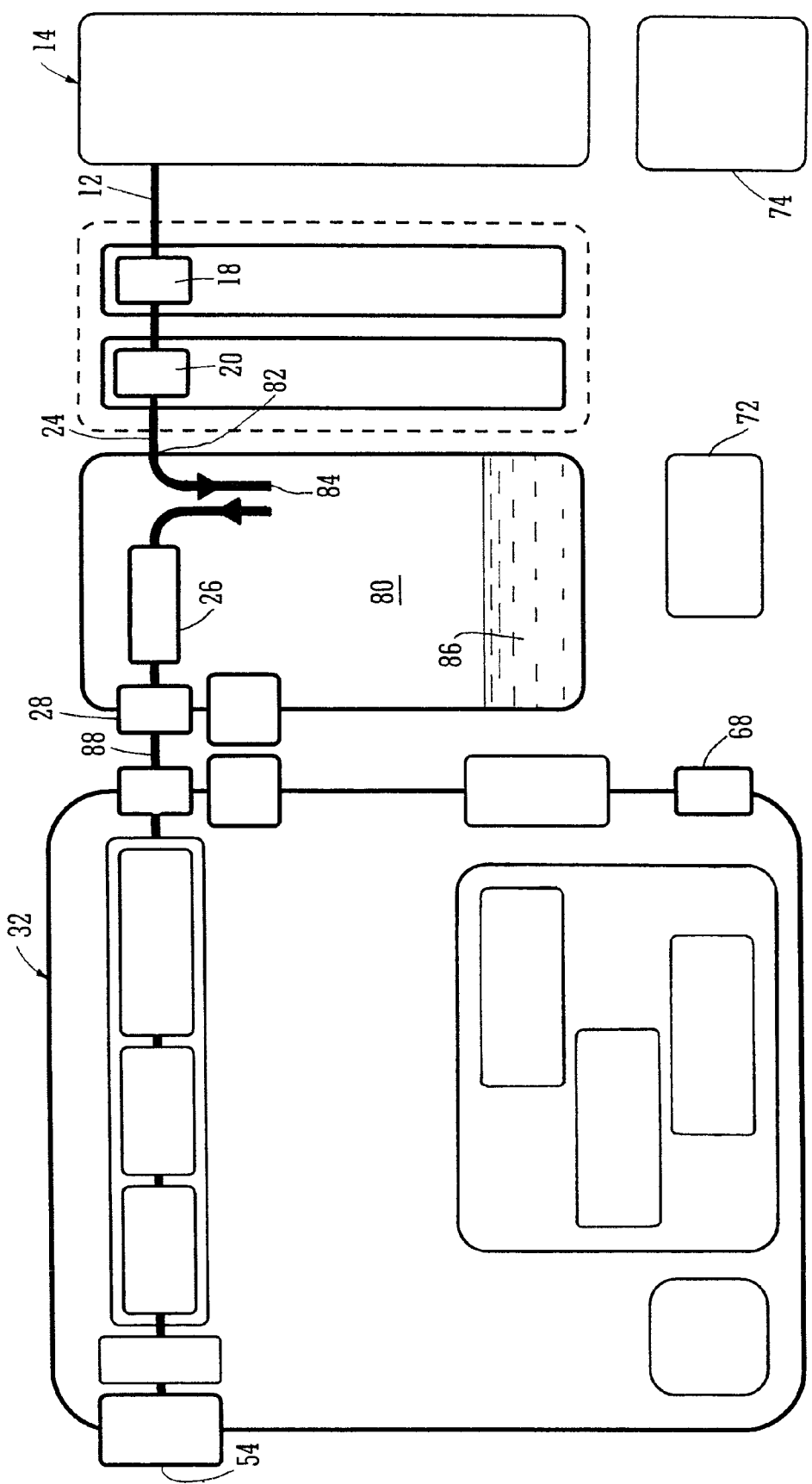
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
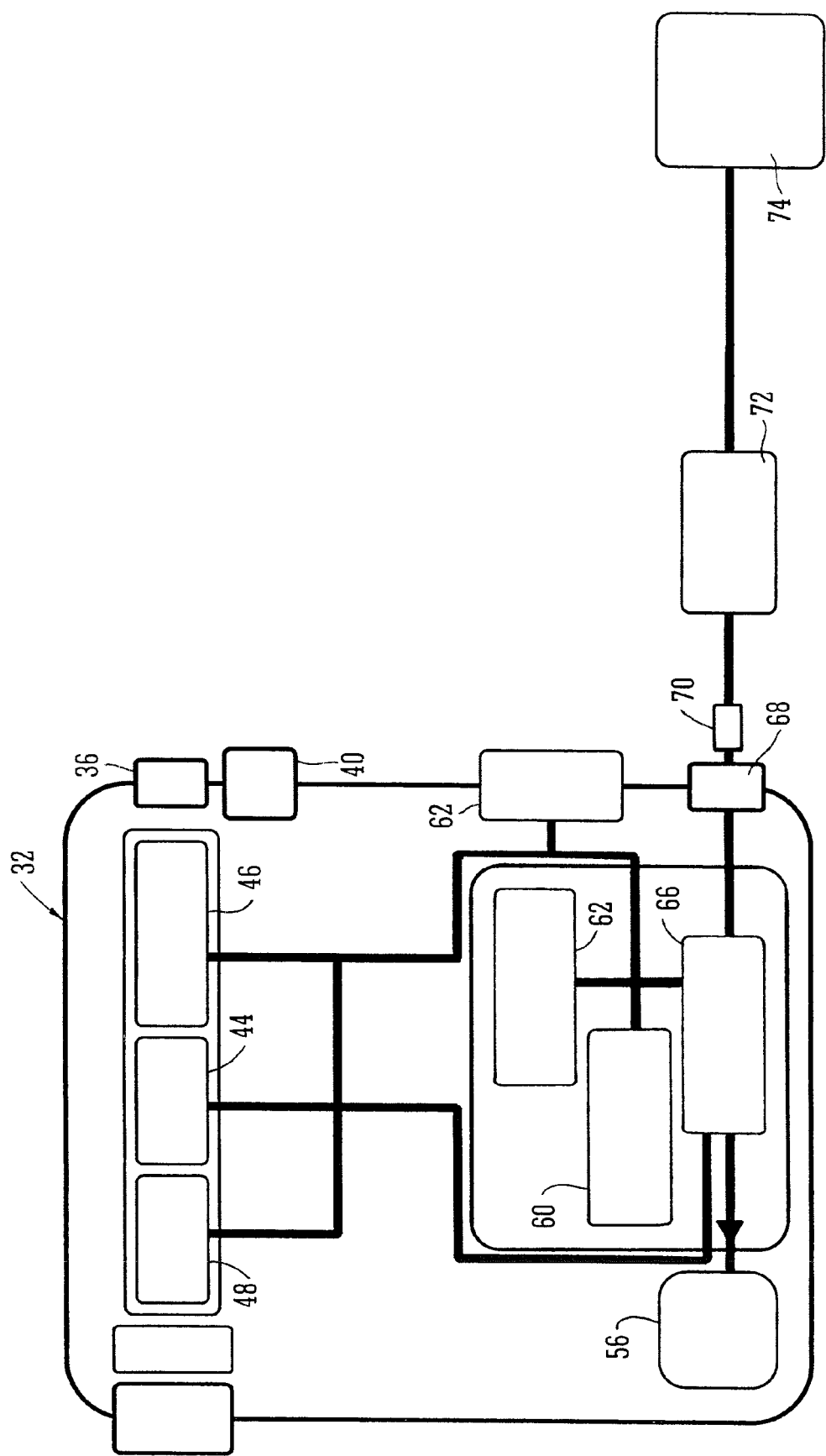
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
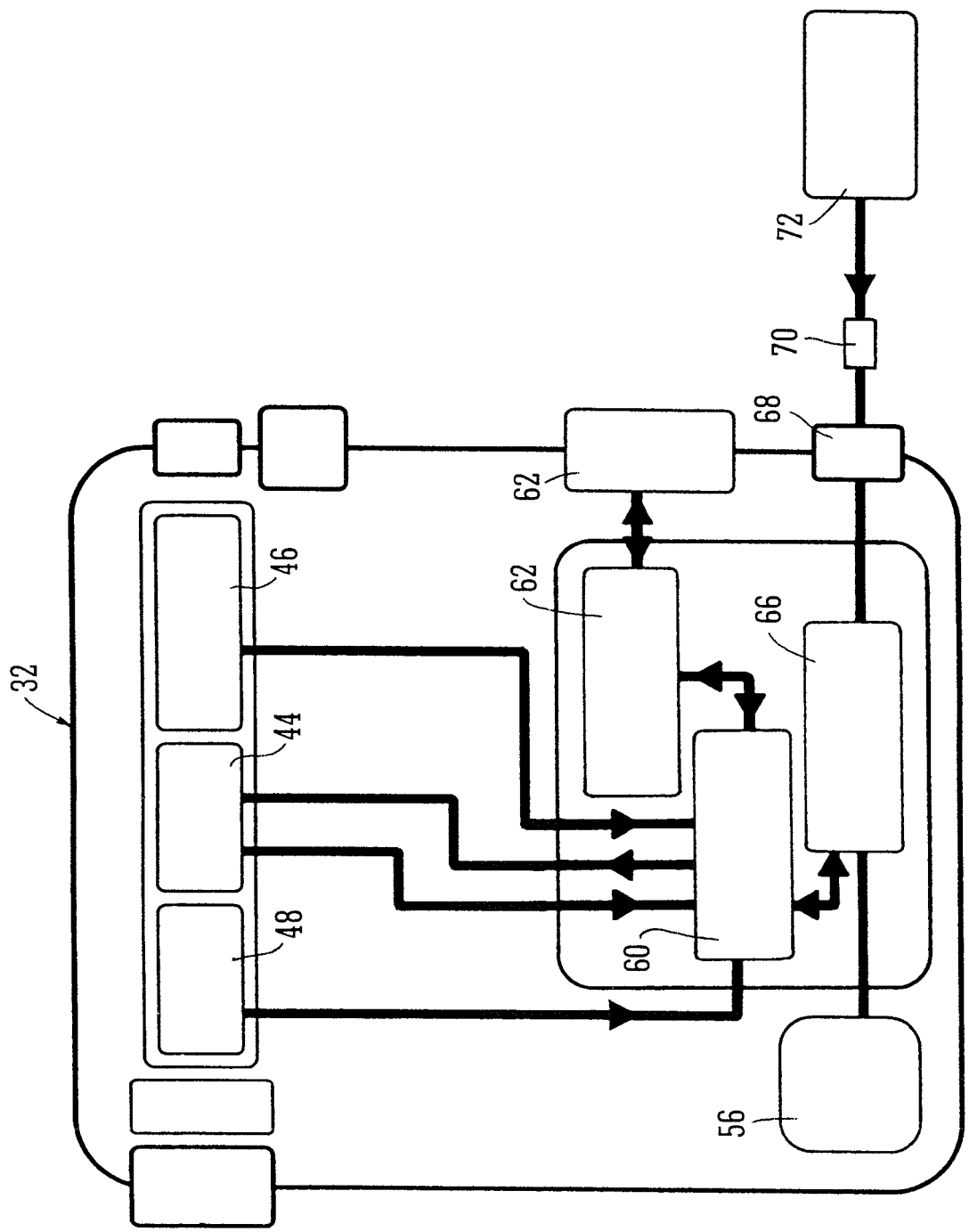
FIG. 4 shows a similar generalised schematic block diagram to FIG. 3 of the device unit and showing control system data paths for controlling the various functions and components of the apparatus.
Figure 5:
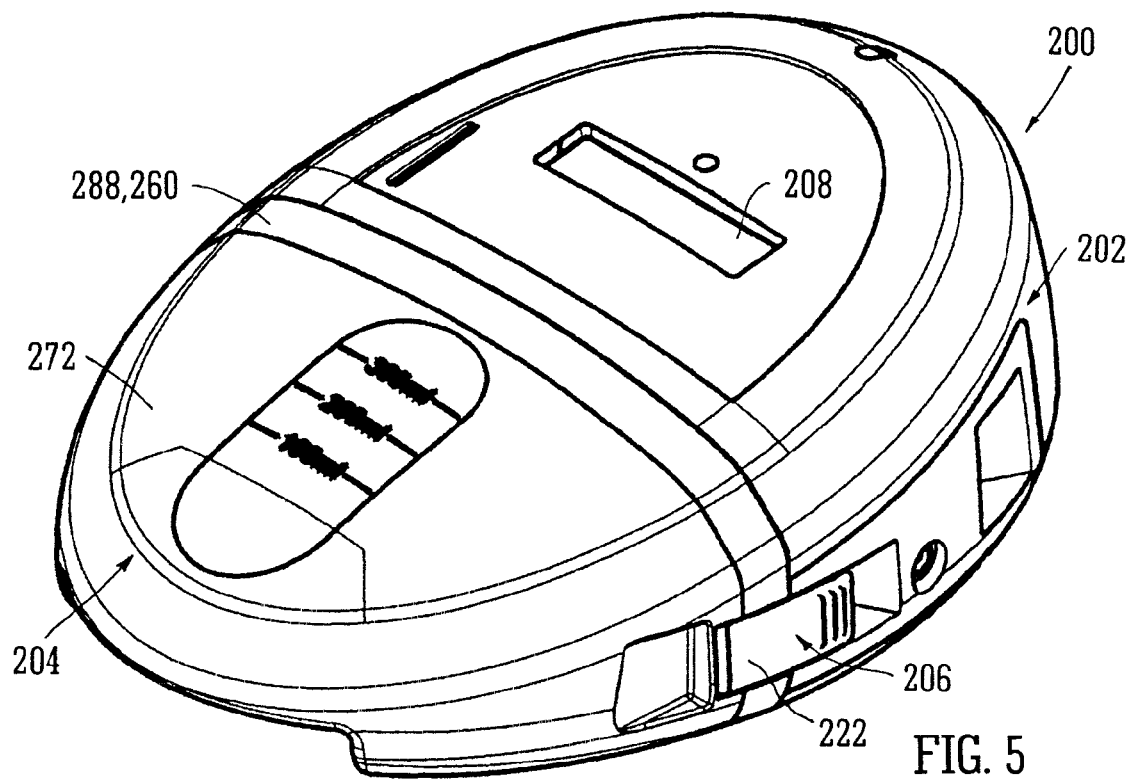
FIG. 5 shows a perspective view of an apparatus.
Figure 6:
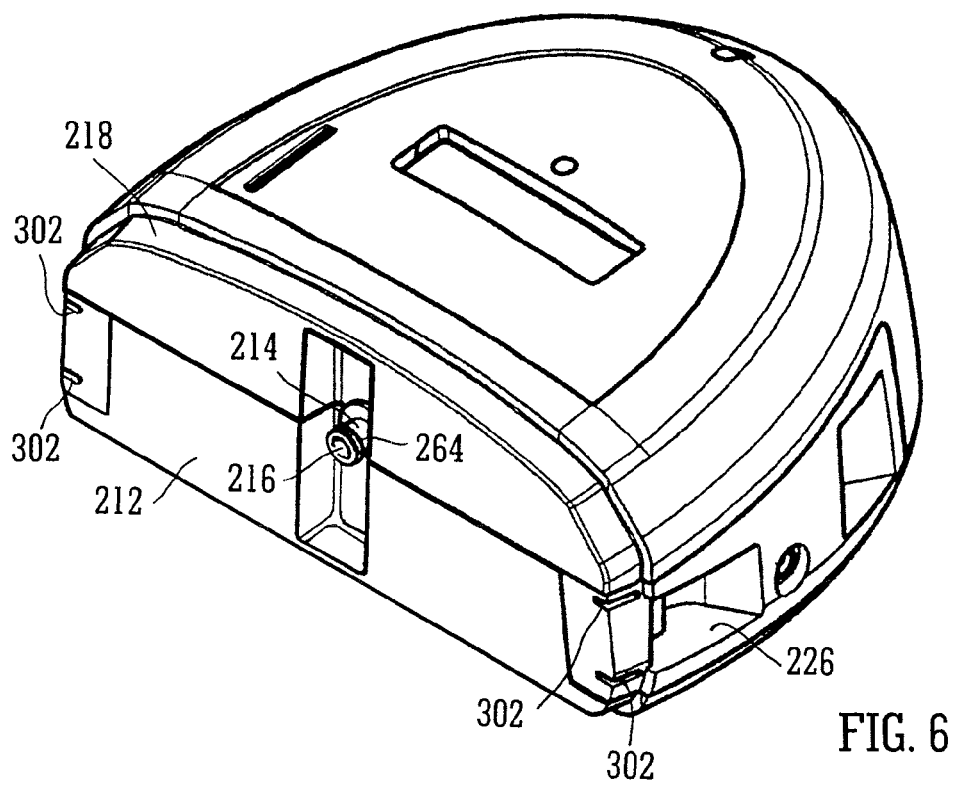
FIG. 6 shows a perspective view of an assembled device unit of the apparatus of FIG. 5.
Figure 7:
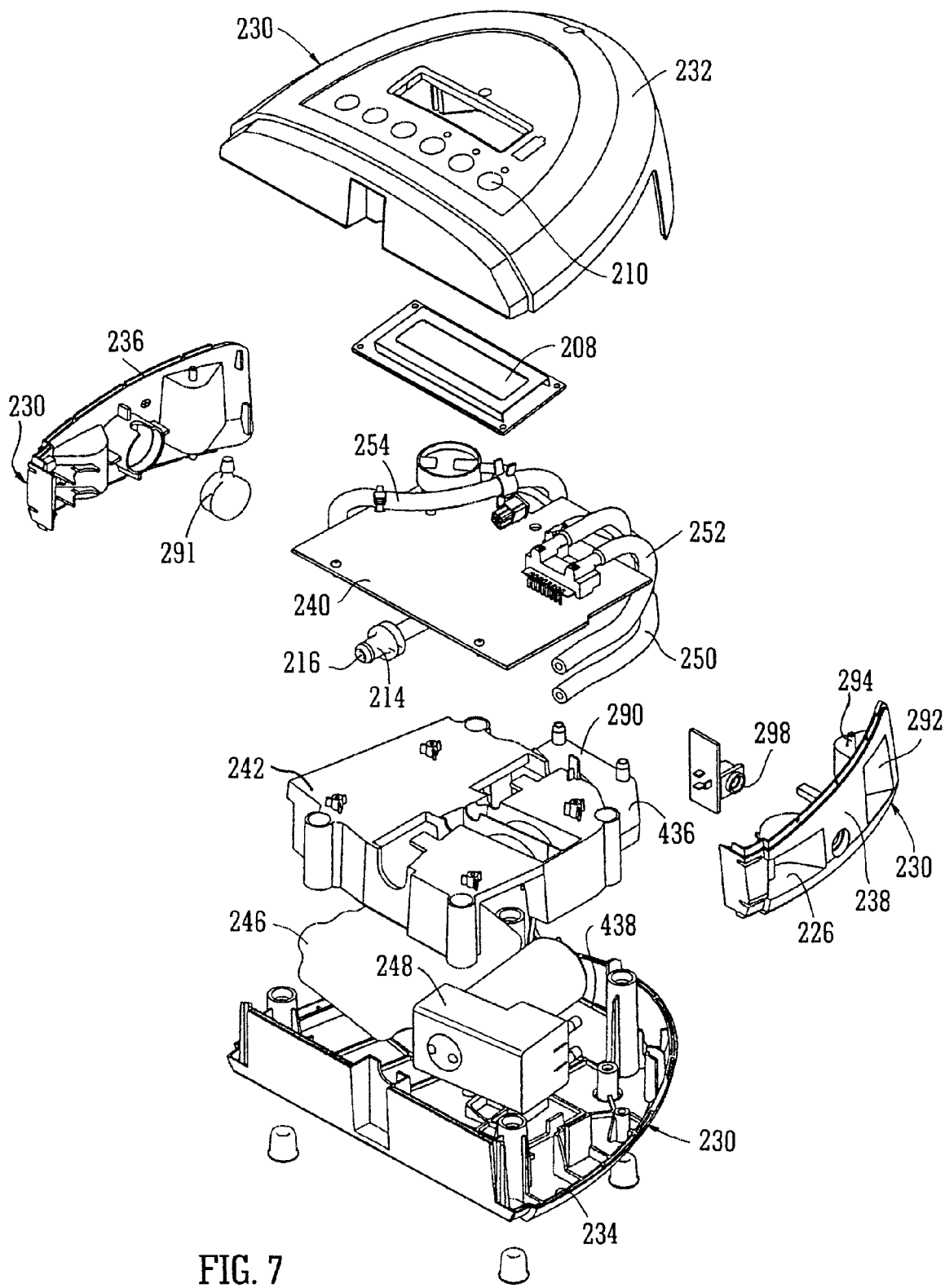
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
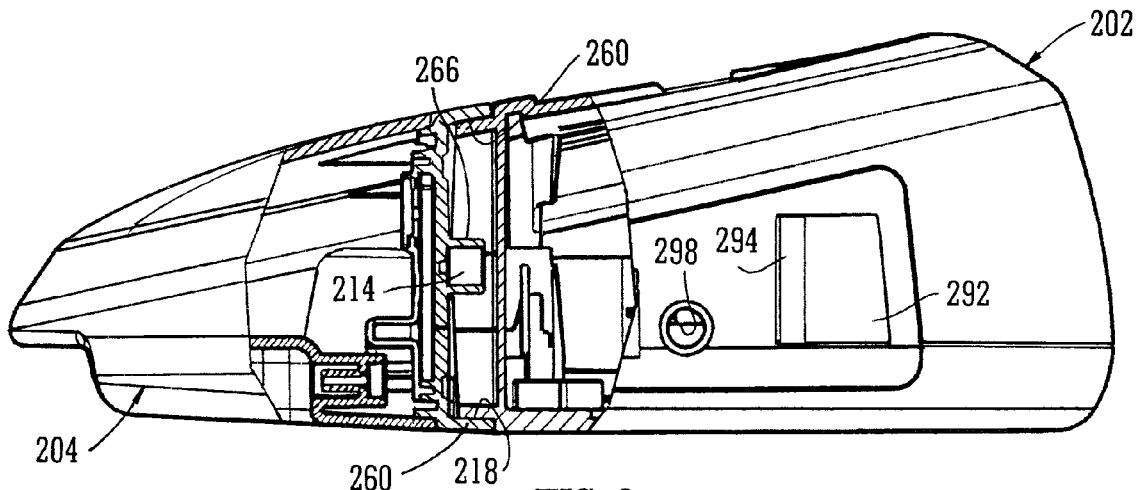
FIG. 8 shows a partially sectioned side elevation view through the interface between a waste canister and device unit of the apparatus.
Figure 9:
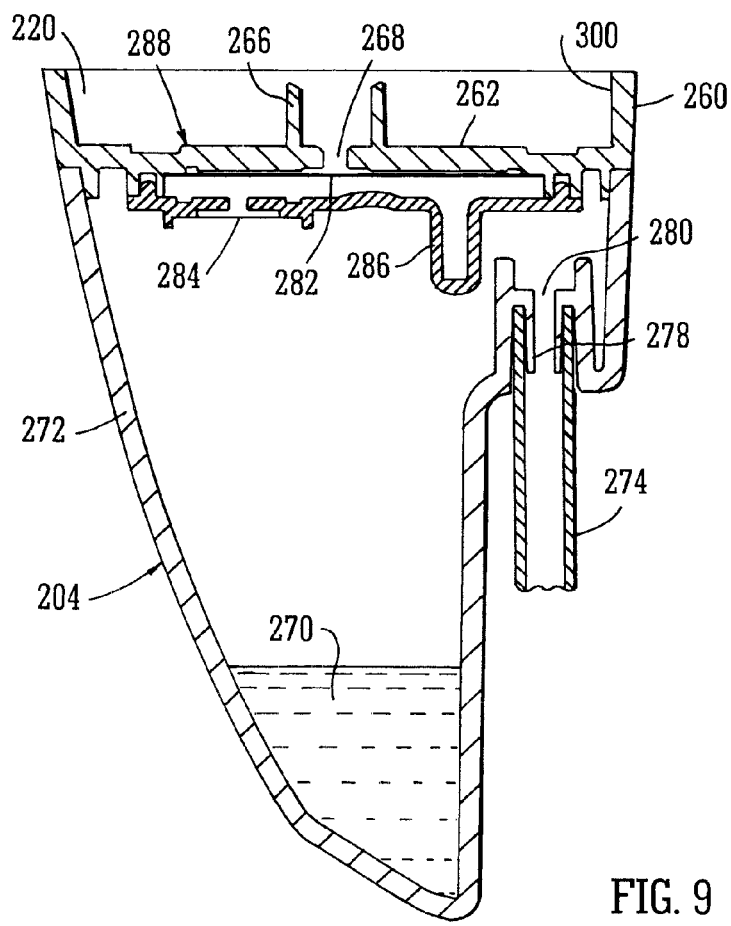
FIG. 9 shows a cross section through a waste canister of the apparatus of FIGS. 5 to 8.
Figure 13:
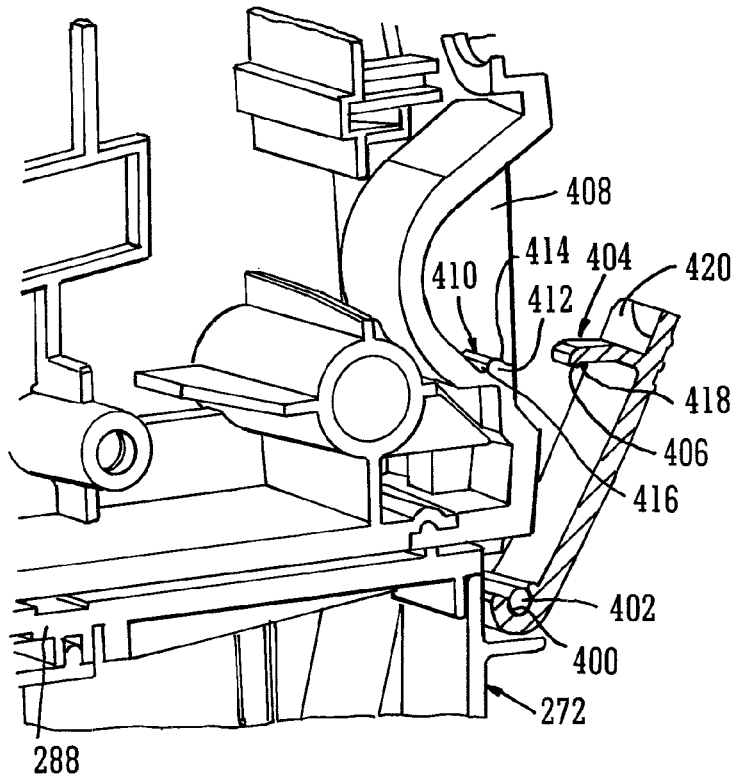
FIG. 13 shows a section through a detail of the junction portion of a device casing and waste canister with a connecting clip about to be engaged.
Figure 14:
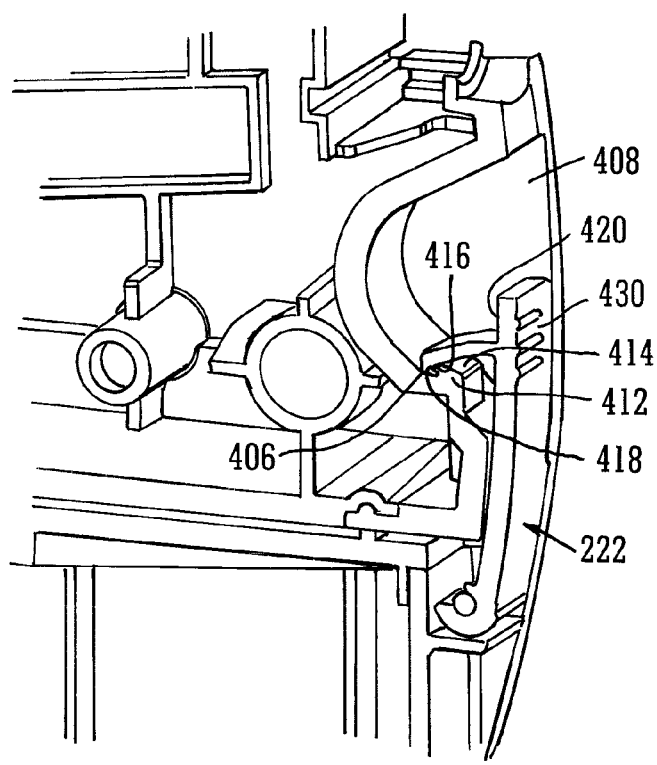
FIG. 14 which shows a section through the same portion of device casing and waste canister as FIG. 13 from a different perspective but with the connecting clip engaged.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by clip arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack (not shown) and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 µm filter and 284 comprising a 1 µm filter are located by a filter retaining member 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet member 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member or bulkhead 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Referring now to FIGS. 10 to 14 wherein a preferred embodiment of the present invention is shown.

In all descriptions of apparatus, right and left are defined as when viewing the apparatus from towards the LCD screen with the device uppermost.

FIG. 10 shows an exploded view of casing parts 230 of the device 202 and waste canister 204: comprising the back moulding 234, left and right-side mouldings 236, 238, respectively of the device; and, the waste canister receptacle portion 272 and closure bulkhead 288. The waste receptacle portion 272 and the closure bulkhead 288 of the waste canister are welded together to form a unitary canister unit. Connecting clip members 222 are provided to connect the waste canister 204 to the device 202. FIGS. 11A and 11B show left and right-hand clips 222 respectively and, although they are different insofar as they are handed, they both possess in principle essentially the same features of construction and function as each other. FIG. 12 shows an enlarged portion of a C-shaped feature 400 which connects the clip member 222 to the waste canister 204 by means of a snap-fit onto a shaft member 402 provided as an integral moulding on the waste canister bulkhead 288. Attachment of the clip member 222 to the shaft 402 is by the C-shaped feature 400 resiliently deforming slightly on pressing onto the shaft 402 before regaining its original size and providing a secure grip on the shaft 402. The clip members 222 also have a finger portion 404 having a downwardly directed lip portion 406, the finger portion being resiliently deformable. The device side insert portions 236, 238 are each provided with a recess 408 (best seen in FIGS. 13 and 14) to accommodate a finger of a user (not shown). When a waste canister is offered up to the device for attachment, the clip 222 is able to rotate through an arc about the shaft 402. At a lower portion of the recess 408 there is a co-operating engaging feature 410 which engages the finger portion 404 and the lip portion 406. The engaging feature 410 comprises an upstanding tooth portion 412 having a sloping lead-in portion 414 which engages with the lip portion 406 causing the finger portion 404 to resiliently deform before snapping into a locking position with a rear face 416 of the lip portion 406 in engagement with a rear face 418 of the tooth 412 so releasably connecting the device 202 and waste canister 204 together. The clip members 222 are also provided with a tactile surface coating 430 such as a soft plastics material on their outer surface which gives a user an intuitive feel when assembling a waste canister to a device.

When the waste canister is to be removed from the device in normal use such as when the canister is full, for example, the user grips a rear face 420 of the clip member 222 above the finger member 404 and pulls in an outwardly direction with their finger. The engaging rear faces 416, 418 of the lip portion 406 and tooth portion 412 are both sloped such that an outwardly force causes the two surfaces 416, 418 to slide relative to each other whilst resiliently deforming the finger portion 404 thus allowing disengagement of the clip member 222 from the device 202 and permitting removal of the waste canister.

Fitting of a new waste canister is simply achieved as explained above.

In the event that the apparatus is subjected to abnormal operating conditions such as, for example, dropping it onto a hard surface from a significant height, perhaps a metre for example, then depending upon the direction of a shock load impinging on the apparatus several possibilities may occur. Firstly, the engaging portion 410 on the device and engaging finger 404 on the clip member may simply disengage due to resilient sliding of the sloped surfaces 416, 418 allowing the device and waste canister to separate or by disengagement of the C-shaped portion 400 from the shaft portion 402. Alternatively, the finger portion 404 may snap off adjacent its root, for example, on the clip member body.

In the event of failure of a clip member by breakage, one or both clip members may simply be replaced by disengaging the C-shaped portion 400 of the broken clip from the shaft portion 402 and fitting a new clip member in its place and reassembling the waste canister to the device as explained above.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. An apparatus for the application of topical negative pressure therapy to a user of the apparatus, the apparatus comprising:
a device;
a waste canister releasably connected to the device; and
one or more clip members configured to extend between the device and the waste canister and to releasably connect the device to the waste canister;
wherein:
the one or more clip members each have a first engagement element configured to disengageably couple with the device and a second engagement element configured to disengageably couple with the canister; and
the clip members are configured to fail in the event of application of an abnormal force to the apparatus.

2. An apparatus according to claim 1, wherein the first engagement element is positioned at or adjacent to a first end portion of at least one of the clip members and the second engagement element is positioned at a second end portion at least one of the clip members.

3. An apparatus according to claim 2, wherein said clip members comprise a metal or plastic, such as polyoxymethylene (POM) acetal polymer.

4. An apparatus according to claim 2, wherein said clip members comprise grip strips to assist the user in engaging said waste canister to said device.

5. An apparatus according to claim 1, wherein
the apparatus comprises a shaft member attached to the canister; and
the second engagement element comprises a resiliently deformable C-shaped recess engageable with the shaft member.

6. An apparatus according claim 1, wherein the clip members are able to withstand a pulling force tending to separate the device and waste canister of at least 20N.

7. An apparatus according to claim 6, wherein the pulling force is about 40N.

8. An apparatus according to claim 6, wherein the pulling force is about 100N.

9. An apparatus according to claim 1, wherein the abnormal force is a force in excess of 100N.

10. An apparatus according to claim 1, wherein said apparatus comprises an alarm that is activated when various abnormal conditions apply.

11. An apparatus according to claim 1, wherein said one or more clip members are releasably attached to the device.

12. An apparatus according to claim 1, wherein said apparatus is portable and further comprises a carry case.

13. An apparatus for the application of topical negative pressure therapy to a user of the apparatus, the apparatus comprising:
a device and a waste canister releasably connected thereto;
wherein:
the device and waste canister are connected together by one or more clip members configured to extend between the device and the waste canister;
the clip members are configured to fail in the event of application of an abnormal force to the apparatus; and
the disengagable feature at the device end is an inwardly turned resiliently deformable finger portion on the clip member which engages with a tooth portion on the device.

14. An apparatus according to claim 13, wherein the finger portion and tooth portion have co-operating inclined surfaces to assist engagement and disengagement between the finger and tooth portions.

15. An apparatus according to claim 13, wherein the clip members are able to withstand a pulling force tending to separate the device and waste canister of at least 20N.

16. An apparatus according to claim 15, wherein the clip members are able to withstand a pulling force tending to separate the device and waste canister of about 40N.

17. An apparatus according to claim 13, wherein said clip members comprise a metal or plastic, such as polyoxymethylene (POM) acetal polymer.

18. An apparatus according to claim 13, wherein said clip members comprise grip strips to assist the user in engaging said waste canister to said device.

19. An apparatus according to claim 13, wherein said apparatus is portable and further comprises a carry case.

20. An apparatus for the application of topical negative pressure therapy to a user of the apparatus, comprising:
   a negative pressure device unit;
   a waste canister releasably connected to the negative pressure device unit; and
   one or more fasteners releasably coupleable to the device unit and the canister, the one or more fasteners being configured to releasably couple the device unit and the waste canister;
   wherein:
      at least one of the clips is configured to releasably engage a shaft member attached to the canister; and
      the fasteners are configured to decouple the device unit from the canister upon the application of an abnormal force on the apparatus.

21. An apparatus according to claim 20, wherein:
   the fasteners comprise clips configured to bridge a junction between the device and the waste canister; and
   the one or more fasteners each have disengagable features at a device end thereof and at a canister end thereof.

22. An apparatus according to claim 21, wherein the disengeagable feature at the canister end comprises a resiliently deformable C-shaped recess releasably coupleable to a shaft portion on said waste canister.

23. An apparatus according to claim 20, wherein at least one of the clips is configured to rotate about the shaft member.

24. An apparatus for the application of topical negative pressure therapy to a user of the apparatus, comprising:
   a device housing a negative pressure pump and controls for said pump; and
   a waste canister releasably connected thereto;
   wherein:
      the device and waste canister are connected together by clips configured to extend between the device and the waste canister on opposite sides of the device;
      the clips have a first end portion attached to the device and a second end portion attached to the waste canister; and
      the clips have one or more points of intended failure configured to break in the event of application of abnormal force to the apparatus, thereby causing the separation of the device and the waste canister; and
      the one or more points of intended failure comprise at least one of a reduced cross-section, a moulded in fracture line, and a finger portion configured to break in the event of the application of abnormal force to the apparatus.

25. An apparatus according to claim 24, wherein said clips have one or more disengeagable features at at least one of the first end portion and the second end portion and are configured to bridge a junction between the device and the waste canister.

26. An apparatus according to claim 25, comprising a disengeagable feature at the second end of at least one of the clips having a resiliently deformable C-shaped recess engageable with a shaft portion attached to said waste canister.

27. An apparatus according to claim 25, comprising a disengeagable feature at the first end of at least one of the clips having an inwardly turned resiliently deformable finger portion configured to engage with a tooth portion on the device.

28. An apparatus according to claim 27, wherein the finger portion and the tooth portion have cooperating inclined surfaces to assist engagement and disengagement between the finger and tooth portions.

29. An apparatus according to claim 24, wherein the one or more points of intended failure comprise a finger portion, and the finger portion contains molded-in fracture lines creating intended weakened points configured to break in the event of application of abnormal force to the apparatus.

30. An apparatus according to claim 24, wherein the one or more points of intended failure comprise a finger portion, and the finger portion is configured to break by snapping off at the root of the finger portion in the event of application of abnormal force to the apparatus.

* * * * *

UNITED STATES PATENT AND TRADEMARK OFFICE
CERTIFICATE OF CORRECTION

PATENT NO. : 8,622,981 B2
APPLICATION NO. : 12/667227
DATED : January 7, 2014
INVENTOR(S) : Hartwell et al.

It is certified that error appears in the above-identified patent and that said Letters Patent is hereby corrected as shown below:

In the Specification

In column 1 at line 4 (approx.), Below "CONNECTION" insert --CROSS-REFERENCE TO RELATED APPLICATIONS This Application is a U.S. National Phase of the International Application No. PCT/GB2008/050508 filed June 27, 2008 designating the U.S. and published on January 8, 2009 as WO 2009/004368, which claims priority of Great Britain Patent Application No. 0712737.6 filed July 2, 2007.

BACKGROUND OF THE INVENTION

Field of the Invention--.

In column 2 at line 19 (approx.), Below "problems." insert --Summary of Some Exemplifying Embodiments--.

In column 6 at line 43 (approx.), Below "which:" insert --Brief Description of the Drawings--.

In column 7 at line 12 (approx.), Below "engaged." insert --Detailed Description of Some Exemplifying Embodiments--.

In column 8 at line 2, Change "the a" to --the--.

In column 9 at line 59, Change "Theses" to --These--.

In the Claims

In column 12 at line 15 (approx.), In Claim 2, change "members" to --members,--.

In column 12 at line 30, In Claim 6, change "according" to --according to--.

In column 12 at line 36, In Claim 8, change "is" to --is less than--.

In column 12 at line 57, In Claim 13, change "the disengagable" to --a disengageable--.

In column 13 at line 31, In Claim 21, change "disengagable" to --disengageable--.

Signed and Sealed this
Eighth Day of July, 2014

Michelle K. Lee
*Deputy Director of the United States Patent and Trademark Office*

CERTIFICATE OF CORRECTION (continued)
U.S. Pat. No. 8,622,981 B2

In column 13 at lines 33-34 (approx.), In Claim 22, change "disengeagable" to --disengageable--.

In column 14 at line 17, In Claim 25, change "disengeagable" to --disengageable--.

In column 14 at lines 21-22, In Claim 26, change "disengeagable" to --disengageable--.

In column 14 at lines 26-27, In Claim 27, change "disengeagable" to --disengageable--.